United States Patent [19]
Hauser et al.

[11] Patent Number: 5,972,346
[45] Date of Patent: Oct. 26, 1999

[54] HEPATITIS B VACCINE

[75] Inventors: Pierre Hauser, Chaumont Gistoux; Nathalie Marie-Josephe Claude Garcon, Wavre; Pierre Desmons, Nivelles, all of Belgium

[73] Assignee: SmithKline Beecham Biologicals S.A., Rixensart, Belgium

[21] Appl. No.: 08/894,643

[22] PCT Filed: Feb. 15, 1996

[86] PCT No.: PCT/EP96/00681

§ 371 Date: Oct. 27, 1997

§ 102(e) Date: Oct. 27, 1997

[87] PCT Pub. No.: WO96/26741

PCT Pub. Date: Sep. 6, 1996

[30] Foreign Application Priority Data

Feb. 25, 1995 [GB] United Kingdom .................. 9503863

[51] Int. Cl.[6] ........................ A61K 39/29; A61K 39/295; A61K 45/00
[52] U.S. Cl. .................... 424/227.1; 424/184.1; 424/201.1; 424/202.1; 424/226.1; 424/228.1; 424/278.1
[58] Field of Search .............................. 424/227.1, 226.1, 424/228.1, 201.1, 202.1, 278.1, 184.1

[56] References Cited

FOREIGN PATENT DOCUMENTS

| | | | |
|---|---|---|---|
| 0414374 | 2/1991 | European Pat. Off. | ........ C07K 15/04 |
| 2 220 211A | 1/1990 | United Kingdom | ........... A61K 37/20 |
| WO 93/19780 | 10/1993 | WIPO | ............................. A61K 39/29 |
| WO 94/21292 | 9/1994 | WIPO | ............................. A61K 39/39 |
| 94/2736 | 12/1994 | WIPO | ............................. A61K 39/12 |

OTHER PUBLICATIONS

Coursajet, et al., Simultaneous Adminstration of Diphtheriz–Tetanus–Pertussis–Polio and Hepatitis B Vaccines . . . , in Infection and Immunity 51(3) pp. 784–787 (1986).

D'Hondt 1992 Vaccine vol. 10 S1 pp. s48–s52, 1992.

Pellegrini, et al., "Preparation and immunogenicity of an inactivated hepatitis A vaccine", *Vaccine*, 11, Issue 3, pp. 383–387 (1993).

Ewasyshyn, et al., "Comparative analysis of the immunostimulatory properties of different adjuvants on the immunogenicity of a prototype parainfluenza virus type 3 subunit vaccine", *Vaccine*, 10, Issue 6, pp. 412–420 (1992).

*Primary Examiner*—Michael P. Woodward
*Assistant Examiner*—Mary K Zeman
*Attorney, Agent, or Firm*—Zoltan Kerekes; Stephen Venetianer; Charles M. Kinzig

[57] ABSTRACT

A novel vaccine formulation is provided, comprising a hepatitis B component, particularly hepatitis B surface antigen, in combination with aluminum phosphate and 3-O-acylated monophosphoryl lipid A.

12 Claims, No Drawings

HEPATITIS B VACCINE

The present invention relates to novel vaccine formulations, methods for preparing them and to their use in therapy. In particular the present invention relates to novel formulations for treating Hepatitis infections and to combination vaccine formulations including a Hepatitis B vaccine component.

Viral hepatitis, caused by the A, B, C, D, and E hepatitis viruses, is a very common viral illness. Via the B and C viruses, in particular, it is also responsible for many cases of liver cancer. Thus the development of effective vaccines is critical and, despite notable successes, is still an on-going task. A review on modern hepatitis vaccines, including a number of key references, may be found in the Lancet, May 12th 1990 at page 1142 ff (Prof A. L. W. F. Eddleston). See also 'Viral Hepatitis and Liver Disease' (Vyas, B. N., Dienstag, J. L., and Hoofnagle, J. H., eds, Grune and Stratton, Inc. (1984) and 'Viral Hepatitis and Liver Disease' (Proceedings of the 1990 International Symposium, eds F. B. Hollinger, S. M. Lemon and H. Margolis, published by Williams and Wilkins).

As used herein the expression 'Hepatitis B antigen' is used to refer to any antigenic material derived from a hepatitis B virus which may be used to induce immunity to the virus in humans.

Infection with hepatitis B virus (HBV) is a widespread problem but vaccines which can be used for mass immunisation are now available, for example the product 'Engerix-B' (SmithKline Beecham plc) which is obtained by genetic engineering techniques.

The preparation of Hepatitis B surface antigen (HBsAg) is well documented. See. for example, Harford et al in Develop. Biol. Standard 54, page 125 (1983), Gregg et al in Biotechnology, 5, page 479 (1987), EP-A-0 226 846, EP-A-0 299 108 and references therein.

As used herein the expression 'Hepatitis B surface antigen' or 'HBsAg' includes any HBsAg antigen or fragment thereof displaying the antigenicity of HBV surface antigen. It will be understood that in addition to the 226 amino acid sequence of the HBsAg S antigen (see Tiollais et al, Nature, 317, 489 (1985) and references therein) HBsAg as herein described may, if desired, contain all or part of a pre-S sequence as described in the above references and in EP-A-0 278 940. In particular the HBsAg may comprise a polypeptide comprising an amino acid sequence comprising residues 12–52 followed by residues 133–145 followed by residues 175–400 of the L-protein of HBsAg relative to the open reading frame on a Hepatitis B virus of ad serotype (this polypeptide is referred to as L*; see EP 0 414 374). HBsAg within the scope of the invention may also include the preS1–preS2-S polypeptide described in EP 0 198 474 (Endotronics) or analogues thereof such as those described in EP 0 304 578 (Mc Cormick and Jones). HBsAg as herein described can also refer to mutants, for example the 'escape mutant' described in WO 91/14703 or European Patent Application Publication Number 0 511 855 A1, especially HBsAg wherein the amino acid substitution at position 145 is to arginine from glycine.

Normally the HBsAg will be in particle form. The particles may comprise for example S protein alone or may be composite particles, for example (L*,S) where L* is as defined above and S denotes the S-protein of HBsAg. The said particle is advantageously in the form in which it is expressed in yeast.

Whilst experimental and commercially available Hepatitis vaccines, for example Engerix-B, afford excellent results it is an accepted fact that an optimal vaccine needs to stimulate not only neutralising antibody but also needs to stimulate as effectively as possible cellular immunity mediated through T-cells. International Patent Application No. WO 93/19780, discloses combination vaccines with a hepatitis B component based on a hepatitis B surface antigen, aluminium hydroxide and 3-de-O-acylated monophosphoryl Lipid A. A formulation comprising aluminium phosphate was not suggested.

Surprisingly, the present invention provides a formulation up to four times more potent than those described in WO 93/19780.

Accordingly the present invention provides a vaccine comprising a hepatitis B antigen in conjunction with 3-O-deacylated monophosphoryl lipid A (abbreviated herein to MPL) and aluminum phosphate.

3-O-deacylated monophosphoryl lipid A (or 3 De-O-acylated monophosphoryl lipid A) has formerly been termed 3D-MPL or d3-MPL to indicate that position 3 of the reducing end glucosamine is de-O-acylated. For preparation, see GB 2 220 211 A Chemically it is a mixture of 3-deacylated monophosphoryl lipid A with 4, 5 or 6 acylated chains. Herein the term 3D-MPL (or d3-MPL) is abbreviated to MPL since 'MPL' is a Registered Trademark of Ribi Immunochem., Montana which is used by Ribi to denote unambiguously their 3-O-deacylated monophosphoryl lipid A product.

Preferably in the compositions of the present invention small particle MPL is used. Small particle MPL has a particle size generally less than 120 nm. Such preparations are described in International Patent Application No. WO 94/21292.

GB 2 220 211A mentions that the endotoxicity of the previously used enterobacterial lipopolysacharides (LPS) is reduced while the immunogenic properties are conserved. However GB 2 220 211 cited these findings merely in connection with bacterial (Gram negative) systems.

Surprisingly, however, it has been found that vaccine compositions according to the invention comprising hepatitis B viral antigens have particularly advantageous properties as described herein.

A particular advantage is that the vaccine formulations of the invention are very effective in inducing protective immunity, even with very low doses of antigen.

The new vaccine formulations allow immunogenicity enhancements equivalent to currently available hepatitis B formulations after two doses. In particular equivalent levels of antibodies were obtained in a human clinical trial after two doses of vaccine compared with three doses of Engerix-B.

They provide excellent protection against primary infection and stimulate advantageously both specific humoral (neutralising antibodies) and also effector cell mediated (DTH) immune responses.

A further important advantage is that vaccine compositions according to the invention may also be used as therapeutic vaccines.

The MPL as defined above will normally be present in the range of 10–100 $\mu$g, preferably 25–50 $\mu$g per dose wherein the Hepatitis B antigen will be typically present in a range 2–50 $\mu$g per dose and the aluminum phosphate will be in the range 500 $\mu$g (Al 3 +) per dose.

An embodiment of the invention is HBsAg S antigen (for example as in Engerix-B) in admixture with MPL and aluminum phosphate as described herein below.

A further specific embodiment of the invention is HBsAg antigen as (L*,S) particles, defined herein above, in admixture with MPL and aluminum phosphate.

The invention in a further aspect provides a vaccine formulation as described herein for use in medical therapy, particularly for use in the treatment or prophylaxis of hepatitis viral infections. In a preferred aspect the vaccine according to the invention is a therapeutic vaccine useful for the treatment of ongoing hepatitis B infections.

In another aspect, the hepatitis vaccine composition of the invention contains other antigens so that it is effective in the treatment or prophylaxis of one or more other bacterial, viral or fungal infections.

Accordingly the hepatitis vaccine formulation according to an embodiment of the invention contains at least one other component selected from other hepatitis antigens, in particular hepatitis A antigen, or non-hepatitis antigens which are known in the art to afford protection against one or more of the following: diphtheria, tetanus, pertussis, Haemophilus influenzae b (Hib), and polio. Antigens against meningitidis A, B, or C may also be included.

Preferably the vaccine according to the invention includes HBsAg as herein above defined.

Particular combination vaccines within the scope of the invention include a DTP (diphtheria-tetanus-pertussis) -hepatitis B combination vaccine formulation, an Hib-Hepatitis B vaccine formulation, a DTP-Hib-Hepatitis B vaccine formulation and an IPV (inactivated polio vaccine) -DTP-Hib-Hepatitis B vaccine formulation.

The hepatitis vaccine or the above combinations may advantageously include a component which is protective against Hepatitis A, especially the killed attenuated strain derived from the HM-175 strain as is present in Havrix.

Suitable components for use in such vaccines are already commercially available and details may be obtained from the World Health Organisation. For example the IPV component may be the Salk inactivated polio vaccine. The pertussis vaccine may comprise whole cell or acellular product, formulated with Diphtheria and Tetanus antigen such as Infanrix DTPa, which comprises three B. pertussis antigens:69 KDa, pertussis Toxin (inactivated), and FHA.

In one aspect the hepatitis or combination vaccine according to the invention may be a paediatric vaccine.

Vaccine preparation is generally described in New Trends and Developments in Vaccines, edited by Voller et al., University Park Press, Baltimore, Md. U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757.

The amount of antigen in each vaccine dose is selected as an amount which induces an immunoprotective response without significant, adverse side effects in typical vaccinees. Such amount will vary depending on which specific antigens are employed. Generally it is expected that each dose will comprise 1–1000 $\mu$g of total antigen, preferably 2–200 $\mu$g. An optimal amount for a particular vaccine can be ascertained by standard studies involving observation of antibody titres and other responses in subjects. Following an initial vaccination, subjects may receive one or more booster doses, for example after 2 and 6 months.

In a further aspect of the present invention there is provided a method of manufacture of a vaccine effective in preventing or treating hepatitis infection, wherein the method comprises mixing the hepatitis antigen as defined herein with aluminum phosphate and MPL.

Using this method one or more additional components are preferably admixed with HBsAg to provide a combination vaccine. Several methods of mixing the components may be used. In one method each antigen may be separately absorbed on aluminum phosphate and after a period of time MPL may be added to each before adding the blending solution.

It will be appreciated that the invention also provides a method of inducing neutralising antibody titres in the range of 10 mU for hepatitis B in a human susceptible to or suffering from hepatitis B infection by administering a composition as herein defined in no more than two doses.

In another aspect, the invention provides the use of a composition as herein defined for the manufacture of a vaccine for the induction of neutralising antibodies in the range of 10 mU for hepatitis B in humans preferably after no more than two doses.

The following examples illustrate the invention and its advantages.

EXAMPLE 1

Hepatitis B vaccine formulation

MPL (3 de-O-acylated monophosphoryl lipid A) was obtained from Ribi Immunochem Research Inc. Aluminum phosphate was obtained from Superphos (Denmark).

MPL was resuspended in water for injection at a concentration varying from 0.2 to 3 mg/ml by sonication until the particles reach a size of between 80 and 200 nm as measured by photo correlation light scattering.

1 to 20 $\mu$g of HBsAg (S-antigen as in Engerix B) in phosphate buffer solution at 0.5 to 3 mg/ml) is adsorbed on 5 to 1000 $\mu$g of aluminum phosphate (solution at 3–6 $Al^{3+}$ mg/ml) for one hour at room temperature under agitation. The mixture was stored at room temperature for 15 days and then maintained at 4° C. before further processing. Then 5 to 200 $\mu$g of MPL (solution 0.2 to 10 mg/ml) were added to the solution. Volume and osmolarity were adjusted to 5 to 1000 $\mu$l with water for injection and saline. Thiomersal (1% w/v) is added up to a final concentration of 0.005% to give the final product.

A similar formulation was prepared by using as the HBsAg component the composite (L*,S) antigen as defined herein above. In this formulation the bacteriostatic agent was 2-phenoxyethanol.

EXAMPLE 2

Clinical studies of Hepatitis B surface antigen formulated with 3 deacylated monophosphoryl lipid A and Aluminium phosphate In clinical testing, various hepatitis B surface antigen containing vaccines were compared. The following groups are considered:

Group 1 HBsAg (20 $\mu$g)/MPL (50 $\mu$g)/AlPO4 (Al:500 $\mu$g)/Thiomersal (50 $\mu$g)/150 mM NaCl/pH 6.1 in 1 ml, formulated as in example 1.

Group 2 HBsAg (20 $\mu$g)/MPL (50 $\mu$g)/Al(OH)3 (Al:100 $\mu$g)/Thiomersal (50 $\mu$g)/10 mM phosphate buffer+150 mM NaCl/pH 6.8 in 1 ml.

Group 3 HBsAg (20 $\mu$g)/MPL (50 $\mu$g)/Al(OH)3 (Al:500 $\mu$g)/Thiomersal (50 $\mu$g)/10 mM phosphate buffer+150 mM NaCl/pH 6.8 in 1 ml.

Group 4 Engerix like
HBsAg (20 $\mu$g)/MPL (0 $\mu$g)/Al(OH)3 (Al:500 $\mu$g)/Thiomersal (50 $\mu$g)/10 mM phosphate buffer+150 mM NaCl/pH 6.8 in 1 ml.

Group 5 HBsAg (20 $\mu$g)/MPL (0 $\mu$g)/AlPO4 (Al:500 $\mu$g)/Thiomersal (50 $\mu$g)/150 mM NaCl/pH 6.1 in 1 ml.

The Volunteers aged 18 to 40 years old were recruited for participation in the trial. Each group (about 60 adults per group at day 0) was vaccinated intramuscularly in the deltoid region at day 0 and 2 months later. A sample of blood was collected before the first injection, one and two months after the first injection and 1, 2 and 4 months after the second injection. The anti-HBs antibodies were measured using the AUSAB kit (Abbott) and a WHO reference calibrated in mlU/ml. Responders had a titre $\geq 1$ ml U/ml. For each time point, the GMT (Geometric Mean Titre) was calculated for seroconverters.

Results

The GMT's are given in Table 1 for each vaccine and table 2 gives the ranking of the antibody titres in each group of vaccinees.

The GMT results (table 1) clearly show that after 2 doses of vaccine containing Al PO4+MPL (group 1), a more than 10 fold increase of the titers is observed after the second dose compared with the titre reached using the commercial Engerix B (group 4). The anti-HBs response is also faster and 51 and 70% of vaccinees have a protective titre (10 ml/U/ml) 1 and 2 months after the first dose (compared to 34 and 16% for Engerix B) (table 2). The addition of 3D-MPL to Engerix B (Group 3), the use of $AlPO_4$ only (group 5) slightly improve the anti-HBS response (compared to Engerix B) but the titres are still 4 to 5 fold lower than with the $AlPO_4$+MPL formulation. Adsorption of HBsAg on a reduced dose of $Al(OH)_3$+MPL gives titres which are similar to those reached with Engerix B. Together, the results indicate that both $AlPO_4$ and MPL are necessary to have an optimal increase of the anti-HBs response in vaccinees after only 2 doses.

TABLE 1

Seroconversion rates (%) and geometric mean anti-HBs antibody titre (GMT) of seroconverters: Preliminary analysis

| Group | Timing | N | S+ | % | GMT | CL 95% lower | CL 95% upper | Min titre | Max titre |
|---|---|---|---|---|---|---|---|---|---|
| 1 | Pre | 59 | 0 | 0.0 | 0 | | | 0 | 0 |
| | PI(m1) | 53 | 46 | 86.8 | 12 | 9 | 8 | 1 | 410 |
| | PI(m2) | 53 | 50 | 94.3 | 18 | 13 | 26 | 1 | 140 |
| | PII(m3) | 53 | 53 | 100.0 | 2092 | 1356 | 3227 | 43 | 60000 |
| | PII(m4) | 39 | 39 | 100.0 | 1613 | 1074 | 2423 | 40 | 19620 |
| | PII(m6) | 25 | 25 | 100.0 | 890 | 582 | 1363 | 42 | 3900 |
| 2 | Pre | 59 | 0 | 0.0 | 0 | | | 0 | 0 |
| | PI(m1) | 53 | 31 | 58.5 | 17 | 10 | 32 | 1 | 1000 |
| | PI(m2) | 53 | 35 | 66.0 | 9 | 6 | 16 | 1 | 860 |
| | PII(m3) | 53 | 35 | 100.0 | 215 | 128 | 360 | 1 | 25000 |
| | PII(m4) | 40 | 40 | 100.0 | 122 | 74 | 201 | 2 | 2808 |
| | PII(m6) | 22 | 22 | 100.0 | 85 | 50 | 145 | 2 | 900 |
| 3 | Pre | 59 | 0 | 0.0 | 0 | | | 0 | 0 |
| | PI(m1) | 53 | 43 | 81.1 | 9 | 6 | 15 | 1 | 720 |
| | PI(m2) | 53 | 44 | 83.0 | 7 | 4 | 10 | 1 | 1040 |
| | PII(m3) | 53 | 53 | 100.0 | 527 | 332 | 838 | 3 | 10100 |
| | PII(m4) | 40 | 40 | 100.0 | 363 | 225 | 586 | 3 | 5638 |
| | PII(m6) | 24 | 24 | 100.0 | 177 | 99 | 316 | 9 | 2196 |
| 4 | Pre | 59 | 0 | 0.0 | 0 | | | 0 | 0 |
| | PI(m1) | 50 | 30 | 60.0 | 11 | 6 | 19 | 1 | 290 |
| | PI(m2) | 50 | 34 | 68.0 | 4 | 3 | 6 | 1 | 45 |
| | PII(m3) | 50 | 50 | 100.0 | 187 | 107 | 329 | 1 | 9500 |
| | PII(m4) | 42 | 42 | 100.0 | 211 | 127 | 350 | 5 | 10584 |
| | PII(m6) | 25 | 25 | 100.0 | 226 | 132 | 386 | 20 | 2595 |
| 5 | Pre | 59 | 0 | 0.0 | 0 | | | 0 | 0 |
| | PI(m1) | 52 | 30 | 57.7 | 12 | 6 | 25 | 1 | 1060 |
| | PI(m2) | 52 | 41 | 78.8 | 9 | 6 | 14 | 1 | 420 |
| | PII(m3) | 52 | 52 | 100.0 | 294 | 168 | 515 | 1 | 18000 |
| | PII(m4) | 41 | 41 | 100.0 | 287 | 158 | 521 | 2 | 15764 |
| | PII(m6) | 24 | 22 | 91.7 | 353 | 188 | 660 | 10 | 7701 |

TABLE 2

Distribution of individual anti-HBs antibody titres preliminary analysis

| Group | Timing | N | >=10 n | % | >=100 n | % | >+1000 n | % |
|---|---|---|---|---|---|---|---|---|
| 1 | Pre | 59 | 0 | 0.0 | 0 | 0.0 | 0 | 0.0 |
| | PI(m1) | 53 | 27 | 50.9 | 2 | 3.8 | 0 | 0.0 |
| | PI(m2) | 53 | 37 | 69.8 | 2 | 3.8 | 0 | 0.0 |
| | PII(m3) | 53 | 53 | 100.0 | 49 | 92.5 | 40 | 75.5 |
| | PII(m4) | 39 | 39 | 100.0 | 37 | 94.9 | 27 | 69.2 |
| | PII(m6) | 25 | 25 | 100.0 | 24 | 96.0 | 15 | 60.0 |
| 2 | Pre | 59 | 0 | 0.0 | 0 | 0.0 | 0 | 0.0 |
| | PI(m1) | 53 | 20 | 37.7 | 3 | 5.7 | 1 | 1.9 |
| | PI(m2) | 53 | 14 | 26.4 | 3 | 5.7 | 0 | 0.0 |
| | PII(m3) | 53 | 50 | 94.3 | 38 | 71.7 | 11 | 20.8 |
| | PII(m4) | 40 | 38 | 95.0 | 24 | 60.0 | 3 | 7.5 |
| | PII(m6) | 22 | 21 | 95.5 | 8 | 36.4 | 0 | 0.0 |
| 3 | Pre | 59 | 0 | 0.0 | 0 | 0.0 | 0 | 0.0 |
| | PI(m1) | 53 | 17 | 32.1 | 7 | 13.2 | 0 | 0.0 |
| | PI(m2) | 53 | 17 | 32.1 | 1 | 1.9 | 1 | 1.9 |
| | PII(m3) | 53 | 51 | 96.2 | 45 | 84.9 | 20 | 37.7 |
| | PII(m4) | 40 | 39 | 97.5 | 34 | 85.0 | 10 | 25.0 |
| | PII(m6) | 24 | 23 | 95.8 | 18 | 75.0 | 3 | 12.5 |
| 4 | Pre | 59 | 0 | 0.0 | 0 | 0.0 | 0 | 0.0 |
| | PI(m1) | 50 | 17 | 34.0 | 3 | 6.0 | 0 | 0.0 |
| | PI(m2) | 50 | 8 | 16.0 | 0 | 0.0 | 0 | 0.0 |
| | PII(m3) | 50 | 46 | 92.0 | 35 | 70.0 | 11 | 22.0 |
| | PII(m4) | 42 | 40 | 95.2 | 30 | 71.4 | 5 | 11.9 |
| | PII(m6) | 25 | 25 | 100.0 | 18 | 72.0 | 4 | 16.0 |
| 5 | Pre | 59 | 0 | 0.0 | 0 | 0.0 | 0 | 0.0 |
| | PI(m1) | 52 | 15 | 28.8 | 5 | 9.6 | 1 | 1.9 |
| | PI(m2) | 52 | 20 | 38.5 | 3 | 5.8 | 0 | 0.0 |
| | PII(m3) | 52 | 48 | 92.3 | 39 | 75.0 | 14 | 26.9 |
| | PII(m4) | 41 | 39 | 95.1 | 31 | 75.6 | 9 | 22.0 |
| | PII(m6) | 24 | 22 | 91.7 | 18 | 75.0 | 5 | 20.8 |

We claim:

1. A vaccine composition comprising a hepatitis B antigen, 3-O-deacylated monophosphoryl lipid A and aluminum phosphate.

2. A vaccine composition as claimed in claim 1 wherein the antigen comprises Hepatitis B surface antigen (HBsAg) or a fragment thereof.

3. A vaccine composition as claimed in claim 2 wherein the antigen is HBsAg and comprises the S antigen of HBsAg.

4. A vaccine composition as claimed in claim 3 wherein the antigen is HBsAg and comprises a pre-S sequence and the S-antigen.

5. A vaccine composition as claimed in claim 3 wherein the HBsAg is a composite particle which contains a modified L protein of hepatitis B virus having an amino acid sequence comprising residues 12–52 followed by residues 133–145 followed by residues 175–400 of the L protein and the S-protein of HBsAg.

6. A vaccine composition as claimed in claim further comprising a component selected from a group consisting of a DTP (diptheria-tetanus-pertussis) HBsAg combination, an Hib-HBsAg combination, a DTP-Hib-HBsAg combination and an IPV (inactivated polio vaccine)-DTP-Hib-HBsAg combination.

7. A vaccine composition as claimed in claim 1 wherein the 3-O-deacylated monophosphoryl lipid A is present in the range 10 $\mu$g–100 $\mu$g per dose.

8. A method of inducing neutralising antibody titres in the range of 10 mU for hepatitis B in a human susceptible to or suffering from hepatitis B infection by administering the vaccine composition as claimed in claim 1.

9. A method of preventing hepatitis B infections in humans which comprises administering an effective amount of a vaccine composition as claimed in claim 1.

10. A method of treating a human subject suffering from an ongoing hepatitis B infection comprising administering an effective amount of a therapeutic vaccine composition as claimed in claim 1.

11. A process for the production of a vaccine composition as claimed in claim 1 comprising absorbing Hepatitis B surface antigen on to aluminium phosphate and then adding 3-O-deacylated monophosphoryl lipid A.

12. A vaccine composition as claimed in claim 4 wherein the HBsAg is a composite particle which contains a modified L protein of hepatitis B virus having an amino acid sequence comprising residues 12–52 followed by residues 133–145 followed by residues 175–400 of the L protein and the S-protein of HBsAg.

\* \* \* \* \*